US007273453B2

(12) United States Patent
Shallenberger

(10) Patent No.: US 7,273,453 B2
(45) Date of Patent: Sep. 25, 2007

(54) METHOD FOR ANALYZING THE BIOLOGICAL AGE OF A SUBJECT

(76) Inventor: Frank Shallenberger, 896 W. Nye La., Suite 103, Carson City, NV (US) 89703

( * ) Notice: Subject to any disclaimer, the term of this patent is extended or adjusted under 35 U.S.C. 154(b) by 304 days.

(21) Appl. No.: 10/943,998

(22) Filed: Sep. 20, 2004

(65) Prior Publication Data

US 2005/0228239 A1    Oct. 13, 2005

Related U.S. Application Data

(63) Continuation-in-part of application No. 10/822,172, filed on Apr. 12, 2004, now abandoned.

(51) Int. Cl.
*A61B 5/00* (2006.01)
*A61B 5/02* (2006.01)
(52) U.S. Cl. .................. 600/300; 600/485; 600/500; 600/529; 600/301
(58) Field of Classification Search .................. None
See application file for complete search history.

(56) References Cited

U.S. PATENT DOCUMENTS

| 5,117,674 | A | 6/1992 | Howard |
| 5,639,471 | A | 6/1997 | Chait |
| 5,660,176 | A | 8/1997 | Iliff |
| 5,705,735 | A | 1/1998 | Acorn |
| 5,810,722 | A | 9/1998 | Heikkilä |
| 5,860,918 | A | 1/1999 | Schradi |
| 5,954,640 | A | 9/1999 | Szabo |
| 5,989,188 | A | 11/1999 | Birkhoelzer |
| 6,074,345 | A | 6/2000 | Van Oostrom |
| 6,126,595 | A | 10/2000 | Amano |
| 6,159,131 | A | 12/2000 | Pfeffer |
| 6,277,072 | B1 | 8/2001 | Bardy |
| 6,280,380 | B1 | 8/2001 | Bardy |
| 6,387,053 | B1 | 5/2002 | Pessenhofer |
| 6,478,736 | B1 | 11/2002 | Mault |
| 6,500,117 | B1 | 12/2002 | Hancock |
| 6,510,430 | B1 | 1/2003 | Oberwager |
| 6,547,729 | B1 | 4/2003 | Abbo |
| 6,554,776 | B1 | 4/2003 | Snow |
| 6,569,624 | B1 | 5/2003 | Weindruch et al. |
| 6,605,038 | B1 | 8/2003 | Teller |
| 6,620,078 | B2 | 9/2003 | Pfeffer |

| 2001/0053883 | A1 | 12/2001 | Yoshimura |
| 2002/0151815 | A1 | 10/2002 | Kawanishi |
| 2002/0193702 | A1 | 12/2002 | Yamazaki |
| 2003/0023145 | A1 | 1/2003 | Lee |
| 2003/0060690 | A1 | 3/2003 | Jellife |
| 2003/0125611 | A1 | 7/2003 | Bardy |
| 2003/0130567 | A1 | 7/2003 | Mault |

FOREIGN PATENT DOCUMENTS

WO         2004/023373     *  9/2003    ............... 600/345

OTHER PUBLICATIONS

Health, Aging, and Disease- Its all about energy—document dated Sep. 16, 2004, obtained at http://smartlifeforum.org/2004/09/newsletter.html.*
Paz, Cerezo M., et al., Influence of Energy Expenditure on Childhood Obesity, Unidad de Gastroenterologia y Nutricion Pediatrica, 58(4), 316-21, Apr. 2003.
Li, J., et al., Influence of Body Fat Distribution on Oxygen Uptake and Pulmonary Performance in Morbidly Obese Females During Exercise, Respirology, 6(1), 9-13, Mar. 2001.
Moon, Jon K, et al., Combined Heart Rate and Activity Improve Estimates of Oxygen Consumption and Carbon Dioxide Production Rates, Journal of Applied Physiology, 81(4), 1754-61, Oct. 1996.
Rumpler, W.V., et al., Repeatability of 24-H Energy Expenditure Measurements in Humans by Indirect Calorimetry, American Journal of Clinical Nutrition, 51(2), 147-152, Feb. 1990.
Schoeller, Dale A., Balancing Energy Expenditure and Body Weight, American Journal of Clinical Nutrition, 68(4), 956S-961S, Oct. 1998.
Bursting With Energy, http://www.burstingwithenergy.com.
Mount Diablo Integrated Wellness, http://www.wcwellness.com/bio.html.
Shallenberger, Bursting With Energy, inMED Publishing, 2002, USA, ISBN 0-9717710-0-6, pp. 32-49.
Bursting With Energy, http://www.burstingwithenergy.com, Sep. 30, 2004.
Mount Diablo Integrated Wellness, http://www.wcwellness.com/bio.html, Sep. 30, 2004.

* cited by examiner

*Primary Examiner*—Robert L. Nasser
(74) *Attorney, Agent, or Firm*—Kramer & Amado, P.C.; Terry W. Kramer; Arlir M. Amado

(57) ABSTRACT

The present invention is a method for analyzing the biological age of a subject. The method analyzes the biological age as it relates to a number of factors indicating levels of health, energy production and metabolism. The method may also be used to calculate a subject's biological age and treat the factors associated with biological age.

23 Claims, No Drawings

METHOD FOR ANALYZING THE BIOLOGICAL AGE OF A SUBJECT

This application is a Continuation-in-Part of U.S. application Ser. No. 10/822,172, filed Apr. 12, 2004, now abandoned, herein incorporated by reference.

BACKGROUND OF THE INVENTION

1. Field of the Invention

This invention relates generally to a method for analyzing the biological age of a subject and treating the subject as a result of the analysis.

2. Description of Related Art

The concept of a biological age is one that has been discussed in longevity and anti-aging literature for many years. It is a measurement or series of measurements that purport to indicate whether or not an individual is aging rapidly or slowly as compared to their chronological age. An accurate analysis of biological age is needed to allow a medical practitioner to create a program to slow down or decrease the aging of a patient and in turn decrease the patient's biological age.

Numerous attempts have been made to quantify biological age in relation to genetics, ethnicity, lifestyle choices and organ function. However none of the prior methods are a true representation of an individual's biological age. Previous attempts do not incorporate the entire range of factors necessary to analyze biological age. Furthermore, biological age can only be properly understood in the context of human aging generally. Therefore the factors that indicate the status of an individual's biological age must be analyzed with respect to similar situated individuals with similar physical characteristics but different ages to understand the biological age of the individual.

SUMMARY OF THE INVENTION

In light of the present need for an accurate method of analyzing the biological age of an individual, a brief summary of the present invention is presented. Some simplifications and omissions may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention includes a method for analyzing the biological age of a subject comprising: obtaining age, body fat percentage, weight and sex information from a subject; measuring the subject's average oxygen consumption when the subject is at rest; measuring the subject's average respiratory exchange ratio when the subject is at rest; measuring the subject's average oxygen consumption when the subject's respiratory exchange rate is about 0.85; measuring the subject's average oxygen consumption when the subject's respiratory exchange rate is about 1.00; measuring the subject's average work produced when the subject's respiratory exchange ratio is about 1.00; calculating the subject's biological age as a function of the subject's average oxygen consumption at rest, the subject's average respiratory exchange ratio when the subject is at rest, the subject's average oxygen consumption when the subject's respiratory exchange rate is about 0.85, the subject's average oxygen consumption when the subject's respiratory exchange rate is about 1.00, and the subject's average work produced when the subject's respiratory exchange ratio is about 1.00; wherein the calculation is dependent on the sex of the subject.

The present invention also includes a method for analyzing the biological age of a subject comprising: obtaining age, body fat percentage, weight and sex information from a subject; measuring the subject's average oxygen consumption when the subject is at rest; measuring the subject's average respiratory exchange ratio when the subject is at rest; measuring the subject's average oxygen consumption when the subject's respiratory exchange rate is about 0.85; measuring the subject's average oxygen consumption when the subject's respiratory exchange rate is about 1.00; measuring the subject's average work produced when the subject's respiratory exchange ratio is about 1.00; analyzing the subject's energy quotient, metabolic rate, resting fat metabolism, exertional fat metabolism and fitness value; and calculating the subject's biological age as a function of the subject's energy quotient, metabolic rate, resting fat metabolism, exertional fat metabolism and fitness value.

The present invention further includes a method for analyzing the biological age of a subject comprising: obtaining age, body fat percentage, weight and sex information from a subject; measuring the subject's average oxygen consumption when the subject's respiratory exchange rate is about 1.00; calculating the subject's predicted maximum oxygen consumption based on the subject's sex, body fat percentage, weight and age in years; wherein the age in years of a subject over a predetermined age is a default age and the age in years of a subject under the predetermined age is the subject's actual age; dividing the subject's average oxygen consumption by the subject's predicted Maximum oxygen consumption to obtain an energy quotient for the subject; and comparing the subject's energy quotient to a target energy quotient range for the subject's appropriate age group.

The present invention further includes a method for analyzing the biological age of a subject comprising: obtaining age, body fat percentage, weight and sex information from a subject; measuring the subject's average resting oxygen consumption; calculating the subject's predicted basal metabolic rate based on the subject's sex, body fat percentage, weight and age in years; wherein the age in years of a subject over a predetermined age is a default age and the age in years of a subject under the predetermined age is the subject's actual age; dividing the subject's average resting oxygen consumption by the subject's predicted basal metabolic rate to obtain a metabolic rate value for the subject; and comparing the metabolic rate value with a target metabolic rate range for the subject's appropriate age group.

The present invention further includes a method for analyzing the biological age of a subject comprising: obtaining age, body fat percentage, weight and sex information from a subject; measuring the subject's resting respiratory exchange ratio; calculating the subject's resting fat metabolism as a function of the subject's resting respiratory exchange ratio; comparing the subject's resting fat metabolism to a target resting fat metabolism range for the subject's appropriate age group; wherein a resting fat metabolism lower than the target resting fat metabolism range indicates increased biological age; and a resting fat metabolism greater than the target resting fat metabolism range indicates optimal biological age.

The present invention further includes a method for analyzing the biological age of a subject comprising: obtaining age, body fat percentage, weight and sex information from a subject; measuring the subject's average oxygen consumption when the subject's exertional respiratory exchange ratio is about 0.85; calculating the subject's predicted maximum oxygen consumption based on the subject's sex, body fat percentage, weight and age in years; wherein the age in years of a subject over a predetermined age is a default age and the age in years of a subject under the predetermined age is the subject's actual age; dividing the subject's average oxygen consumption when the subject's respiratory exchange rate is about 0.85 by the subject's predicted maximum oxygen consumption to obtain an exertional fat metabolism for the subject; and comparing the subject's exertional fat metabolism to a target exertional fat metabolism range for the subject's appropriate age group.

The present invention also includes a method for analyzing the biological age of a subject comprising: obtaining age, body fat percentage, weight and sex information from a subject; measuring the subject's average work produced when the subject's exertional respiratory exchange ratio is about 1.00; calculating the subject's predicted maximum oxygen consumption based on the subject's sex, body fat percentage, weight and age in years; wherein the age in years of a subject over a predetermined age is a default age and the age in years of a subject under the predetermined age is the subject's actual age; calculating the subject's predicted maximum work produced as a function of the subject's predicted maximum oxygen consumption; dividing the subject's average work produced when the subject's exertional respiratory exchange ratio is about 1.00 by the subject's predicted maximum work produced to obtain an overall fitness value for the subject; and comparing the subject's overall fitness value to a target overall fitness range for the subject's appropriate age group.

DETAILED DESCRIPTION OF THE PREFERRED EMBODIMENTS OF THE INVENTION

The present invention describes a method for analyzing the biological age of a subject. This method is required for both analyzing the multiple factors that present an overall view of the biological age of a patient and for treating the various factors to improve the biological age of a patient.

A number of factors make up the total understanding of the biological age of a patient. These factors are determined through a number of measurements taken from the patient by a medical practitioner. The measurements may include both physical characteristics and breath-by-breath measurements. The physical characteristics of the patient may include: the subject's age, height, weight, sex, supine and standing blood pressures, and body fat percentage as determined by a bio-impedance measurement. The breath-by-breath measurements are taken using a specialized device such as a pulmonary gas exchange analyzer. The breath-by-breath measurements may include: oxygen consumption while resting; oxygen consumption during exercise; carbon dioxide production while resting; carbon dioxide production during exercise; work as measured in watts during exercise; heart rate while resting; heart rate during exercise; and respiratory rate while resting.

The breath-by-breath measurements may then be used to prepare a number of data points relating to the factors used for analyzing biological age. These data points may include: average resting oxygen consumption; average resting respiratory exchange ratio; average resting heart rate; average resting respiratory rate; average resting end tidal CO2 percentage, average resting carbon dioxide production; anaerobic threshold (the point at which the respiratory exchange ratio is equal to about 1.00 on average); exertional average oxygen consumption at anaerobic threshold; average amount of work in watts at anaerobic threshold, average heart rate at anaerobic threshold; the point at which the patient's respiratory exchange rate is equal to 0.85 on average; average exertional oxygen consumption when the respiratory exchange ratio is equal to 0.85; and average heart rate when the respiratory exchange ratio is equal to 0.85.

In order to provide a more exact analysis of the patient's biological age, it is a preferred embodiment of the invention to take breath-by-breath readings according a specific protocol which removes erroneous information. The preferred embodiment includes recording all breath samplings, respiratory rate and heart rate measurements for a continuous interval of seven minutes while the subject is at rest. The best five of seven averages are computed and recorded every 15 second interval for heart rate, respiratory rate, respiratory exchange ratio, and average oxygen consumption. The readings taken during the first minute are rejected. The remaining readings are designated as resting readings. Of these resting readings, all average oxygen consumption readings greater than a predicted BMR divided by 5.5 are removed, and all values less than predicted BMR divided by 11 are removed. The predicted BMR is calculated depending on sex. For men the predicted BMR=66.4730+(13.7516×weight)+(5.0033×Height)−(6.7550×Age). For women the predicted BMR=655.0950+(9.536×weight)+(1.8496×height)−(4.6756×Age). After resting average oxygen consumption readings have been removed based on the subject's corresponding BMR, the remaining two highest and lowest values are removed. The remaining values are designated as "Remaining Resting Oxygen Consumption Readings" and are used to determine other measuring points. In the event that the number of Remaining Resting Oxygen Consumption Readings is less than five, the above calculation is modified so that all resting average oxygen consumption readings greater than a predicted BMR divided by 4.0 are removed, all values less than predicted BMR divided by 11 are removed, and the remaining two highest and lowest values are removed. In this case, the newly determined Remaining Resting Oxygen Consumption Readings are then used to determine the following measuring points:

Resting Average Oxygen Consumption (RVO2): The resting average oxygen consumption is determined by the equation: RVO2=((2×lowest remaining resting oxygen consumption reading)+highest remaining resting oxygen consumption reading)/3

Resting Respiratory Exchange Ratio (RRER): The resting respiratory exchange ratio is the average ratio of carbon dioxide produced to oxygen consumed while the subject is at rest. In a preferred embodiment of the invention those respiratory exchange ratios not associated with Remaining Resting Oxygen Consumption Readings are removed, and those respiratory exchange ratios greater than 0.95 and less than 0.72 are also removed. The remaining ratios are the "Remaining Respiratory Exchange Ratio Readings." The average of the Remaining Respiratory Exchange Ratio Readings gives the Resting Respiratory Exchange Ratio. In the event that the Remaining Respiratory Exchange Ratio Readings number less than five, the above calculation is modified so that respiratory exchange readings greater than 0.95 are not removed in determining the Remaining Respiratory Exchange Ratio Readings. In this case the average of the newly determined Remaining Respiratory Exchange Ratio Readings are used to compute the Resting Respiratory Exchange Ratio.

In another preferred embodiment of the invention, a protocol for removing erroneous data is also applied to the breath-by-breath readings taken while the subject is exercising. In the preferred embodiment, the best five of seven averages are computed and recorded every 15 second interval for heart rate, respiratory exchange ratio, and oxygen consumption. The first minute of data points are removed, and the remaining readings are the exercise readings. The fat burning heart rate is equal to one half of the sum of the highest heart rate and the lowest heart rate determined between the minimum respiratory exchange rate greater than or equal to 0.82 and the maximum respiratory exchange rate less than or equal to 0.88 in the exercise readings. When there is no RER less than or equal to 0.88 in the exercise readings, the FBR is equal to the average of the first five heart rates in the exercise readings. The fat burning work range in the exercise readings is determined between the first heart rate when approaching from the lower numbers greater than or equal to the fat burning heart rate−2 and the first heart rate when approaching from the higher numbers less than or equal to the fat burning heart rate+2. The anaerobic threshold heart rate is equal to one half of the sum of the highest heart rate and the lowest heart rate determined between a minimum second respiratory exchange rate greater than or equal to 0.98 and a maximum second respiratory exchange rate less than or equal to 1.02 in the exercise readings. The anaerobic threshold work range in the exercise readings is determined between the first heart rate when approaching from the lower numbers greater than or equal to the anaerobic threshold heart rate−2 and the first heart rate when approaching from the higher numbers less than or equal to the anaerobic threshold heart rate+2.

In a preferred embodiment of the invention, the data points determined above are further used to calculate the following measurements:

The subject's average oxygen consumption when the when the subject is exerting at a respiratory exchange rate of about 0.85 (RER.85VO2) is equal to one half of the sum of the highest and lowest oxygen consumption values found in the fat burning work range.

The subject's average oxygen consumption when the subject is exerting at a respiratory exchange ratio of about 1.00 (ATVO2) is equal to one half of the sum of the highest and lowest average oxygen consumptions in the anaerobic threshold work range.

The subject's average amount of work produced (as measured in watts) when the subject is exerting at a respiratory exchange ratio of about 1.00 (ATWORK) is equal to one half of the sum of the highest and lowest work values found in the anaerobic threshold work range.

These data points are then used to assess the factors relating to the biological age of the subject. These factors include, but are not limited to, the energy quotient of the subject, the basal metabolic rate of the subject, the resting fat metabolism of the subject, the exertional fat metabolism of the subject, and the overall fitness of the subject. These factors may also be used to compute the biological age of the subject.

In an embodiment of the invention, the method includes analyzing the biological age of a subject as it relates to the energy quotient of the subject. In a preferred embodiment, the energy quotient of the subject is equal to the average oxygen consumption of the subject at a respiratory exchange ratio of about 1.00 divided by the predicted maximum oxygen consumption for the subject.

The predicted maximum oxygen consumption for a person is determined based on the age, sex, weight, and body fat percentage of the patient as follows: predicted maximum oxygen consumption for a male=[weight (in kilograms)×(1−(body fat percentage/100))/0.82]×(50.72−(0.372×age)). Predicted maximum oxygen consumption for a female= ([weight (in kilograms)×(1−(body fat percentage/100))/ 0.78]+43)×(22.78−(0.17×age)).

Accurately analyzing the biological age of a subject requires taking the equations for calculating predicted maximum oxygen consumption and adjusting them for age. In a preferred embodiment of the invention, when calculating predicted maximum oxygen consumption for a subject whose actual age in years is over a predetermined age, a default age is used instead. In a more preferred embodiment of the invention, the predetermined age is 35-60. In a further preferred embodiment, the predetermined age is forty (40). The predetermined age is chosen as the age at which individuals generally first begin to show signs of biological aging. Therefore if the general population begins to age either more quickly or more slowly, the predetermined age may also change accordingly. The predetermined age and default age may be different. In a further preferred embodiment of the invention, the predetermined age is equal to the default age. In another preferred embodiment, when calculating predicted maximum oxygen consumption for a subject whose actual age is under forty (40), the actual age of the subject is used. A further preferred embodiment may be illustrated by the following examples: For a subject with actual age greater than the predetermined age: Subject's actual age is 50, greater than the predetermined age of 40, a default age of 40 is used to calculate the subject's predicted maximum oxygen consumption. For a subject with actual age less than the predetermined age: Subject's actual age is 35, lower than the predetermined age of 40, the subject's actual age of 35 is used to calculate the subject's predicted maximum oxygen consumption.

Once the average oxygen consumption at anaerobic threshold of an individual is divided by the individual's predicted maximum oxygen consumption, the number is multiplied by 166.66 to assess the individual's energy quotient. An energy quotient greater than 100 is the goal of every patient. The goal of patients under fifty years old is to achieve an energy quotient greater than 120. Persons older than 60 to 70 years of age should target an energy quotient greater than 100. By applying the patient's energy, quotient to these ranges, the biological age of the patient may be determined where an energy quotient lower than the target energy quotient range indicates increased biological age; and wherein an energy quotient greater than the target energy quotient range indicates optimal biological age.

Accurately assessing the energy quotient of a subject allows a practitioner to begin to treat and reduce the biological age of the subject. Therefore, another embodiment of the invention includes treating the biological age of a subject. A low energy quotient can result from a number of factors related to the biological aging of the subject. These factors may include disease, nutrition and exercise. In particular, a physician may treat heart, lung and breathing related disease using conventional means to improve the patient's energy production. In a preferred embodiment of the invention, a physician may also prepare and administer a nutrition and exercise program to a patient in order to improve his or her energy quotient. In a preferred embodiment, a nutrition program may include decreased caloric intake, decreased dietary carbohydrate intake, nutritional supplementation, hormonal replacement, therapeutic detoxification, and medication. In another preferred embodiment, an exercise program may include zone interval training and/or zone circuit training, wherein the levels described as "regular intensity" and "high intensity" are determined by the subject's energy quotient. Zone interval training is defined as an exercise regimen where a subject exercises at regular intensity then intersperses intervals of high intensity exercise for a predetermined period of time. Zone circuit training combines interval training with multiple repetitions of resistance training exercise for a predetermined period of time. In a preferred embodiment of the invention, periods for zone interval training and zone circuit training are used to improve a subject's energy quotient. Furthermore, both the nutritional program and exercise program may be combined to maximize treatment of a patient's energy quotient.

In another embodiment of the invention, the method is used to analyze the biological age of a subject as it relates to the basal metabolic rate of the subject. The subject's "metabolic rate value" is determined as a function of the subject's average resting oxygen consumption and the predicted basal metabolic rate of the subject.

In a preferred embodiment of the invention, the predicted basal metabolic rate is calculated based on the sex of the subject. In a preferred embodiment the predicted metabolic rate for males is equal to $66.4730+(13.7516\times\text{weight})+(5.0033\times\text{height})-(6.7550\times\text{age})$. In another preferred embodiment the predicted metabolic rate for females is equal to $655.0950+(9.536\times\text{weight})+(1.8496\times\text{height})-(4.6756\times\text{age})$. In a preferred embodiment of the invention, when calculating predicted basal metabolic rate for a subject whose actual age in years is over a predetermined age, a default age is used instead. In a more preferred embodiment of the invention, the predetermined age is 35-60. In a further preferred embodiment, the predetermined age is 40. The predetermined age is chosen as the age at which individuals generally first begin to show signs of biological aging. Therefore if the general population begins to age either more quickly or more slowly, the predetermined age may also change accordingly. The predetermined age and default age may be different. In a preferred embodiment of the invention, the predetermined age is equal to the default age. In another preferred embodiment, when calculating, predicted basal metabolic rate for a subject whose actual age is under forty, the actual age of the subject is used.

In a preferred embodiment, the equation for calculating metabolic rate value (MRV) is equal to $6.95\times$ average resting oxygen consumption (RVO2) multiplied by 100 and divided by the predicted basal metabolic rate. In a further preferred embodiment, the target range for a subject's MRV is 100-120. An MRV in this range shows optimal metabolic rate and results in an optimal biological age. An MRV below this range shows a low metabolic rate and results in an increased biological age. An MRV below the target range may also be indicative of a number of other health deficiencies or other issues including, but not limited to: adrenal insufficiency, thyroid deficiency, insufficient sleep, deficient muscle mass, testosterone deficiency, growth hormone deficiency, nutritional deficiency, excessive estrogen, progesterone deficiency, and dehydration. An MRV >120 may indicate a hyper-metabolic conditions including, but not limited to, hyperthyroidism, pain, fever, and certain disease states.

Another embodiment of the invention includes analyzing biological age as it relates to the resting fat metabolism of a subject. In a preferred embodiment of the invention, the resting fat metabolism of a subject is analyzed as a function of the subject's resting respiratory exchange ratio (RRER). In a further preferred embodiment, the resting fat metabolism (RFM) is equal to $283.52-(\text{resting respiratory exchange ratio}\times235.29)$.

In a preferred embodiment of the invention, a RFM of greater than 100 indicates optimal fat metabolism which results in optimal biological age. Alternatively, a RFM of less than 100 is indicative of sub-optimal fat metabolism which results in increased biological age. In a further preferred embodiment of the invention, sub-optimal resting fat metabolism and increased biological age are treated by prescribing a diet restricting carbohydrates and increasing nutritional supplementation. Extreme cases of low resting fat metabolism may require therapeutic detoxification, hormonal replacement and/or other medical intervention.

In another preferred embodiment of the invention, the method is used to analyze biological age as it relates to the exertional fat metabolism of a subject. In a further preferred embodiment, exertional fat metabolism of a subject is calculated by dividing the subject's average oxygen consumption when the subject is exerting at a respiratory exchange ratio of about 0.85 (RER.85VO2) by the subject's predicted maximum oxygen consumption.

In a preferred embodiment of the invention, the subject's exertional fat metabolism value (EFM) is calculated as $238\times(\text{RER.85VO2})/(\text{predicted maximum oxygen consumption})$. In a preferred embodiment of the invention, a target EFM range is >100. In a further preferred embodiment of the invention, an EFM greater than or equal to 100 indicates optimal exertional fat metabolism, which results in optimal or decreased biological age. In another further preferred embodiment of the invention, an EFM less than 100 indicates decreasing exertional fat metabolism, which results in increased biological age. An EFM significantly less than 90 may indicate diabetes, insulin resistance, excessive carbohydrate intake, hormonal deficiencies, excessive trans fatty acids, nutritional deficiencies and/or additional health deficiencies. A further preferred embodiment of the invention may include treating decreased exertional fat metabolism by prescribing nutritional supplementation, dietary restrictions, and/or other medical treatments.

Another embodiment of the invention includes a method for analyzing biological age as a factor of a subject's overall fitness. In a preferred embodiment of the invention, the subject's overall fitness is calculated as the subject's average work produced when the subject's exertional respiratory rate exchange ratio is about 1.00 (ATWORK) divided by the subject's predicted maximum work produced. In a preferred embodiment of the invention, the subject's predicted maximum work produced for a male is equal to (predicted maximum oxygen consumption$-(5.8\times[\text{weight (in kilograms)}\times(1-(\text{body fat percentage}/100))/0.82])-151)/10.1$ and for a female is equal to (predicted maximum oxygen consumption$-(5.8\times[\text{weight (in kilograms)}\times(1-(\text{body fat percentage}/100))/0.78])-151)/10.1$. The predicted maximum oxygen consumption is calculated as shown above.

In a preferred embodiment of the invention, the subject's overall fitness value (FV) is equal to $125\times(\text{ATWORK})$ divided by the subject's predicted maximum work produced. The subject's predicted maximum work produced is described in detail above.

In a preferred embodiment of the invention, a target FV is >100. In a further preferred embodiment, an FV greater than or equal to 100 indicates optimal strength and fitness which results in optimal biological age. In another preferred embodiment of the invention, an FV less than 100 indicates decreased strength and fitness which results in increased biological age. An FV significantly lower than 100 may indicate decreased muscle mass or sarcopenia. A preferred embodiment of the invention may include a method for treating decreased strength and fitness by prescribing nutritional supplementation, hormonal replacement, and an exercise regimen. The exercise regimen may include resistance training and/or aerobic exercise.

In another embodiment of the invention, the medical practitioner analyzes the subject's biological age by directly calculating the biological age as it relates to the biological aging process of the individual. In a preferred embodiment of the invention, a subject's biological age is calculated as follows: Biological Age/male=0.33 {BAeq/male+2(BAeq/male)/[0.0016(RFM+EFM)+0.0033(MRV)+0.0033(FV)]} and Biological Age/female=0.33{BAeq/female+2(BAeq/female)/[0.0016(RFM+EFM)+0.0033(MRV)+0.0033(FV)]}.

In these equations the following abbreviations apply:

RFM=resting fat metabolism value if resting fat metabolism value <100, and =100 if resting fat metabolism value >100

EFM=exertional fat metabolism value if exertional fat metabolism value <100, and =100 if exertional fat metabolism value >100

MRV=metabolic rate value if metabolic rate value <100, and =100 if metabolic rate value >100

FV=overall fitness value if overall fitness value <100, and =100 if overall fitness value >100

BAeq/male=136−0.96×energy quotient

BAeq/female=136−0.93×energy quotient

In addition, when the subject's Biological Age is calculated to be greater than 100 it defaults to 100. When the subject's Biological Age is calculated to be less than 30 it defaults to 30.

By applying these equations, the practitioner can see that an individual with an energy quotient, metabolic rate value, resting fat metabolism value, exertional fat metabolism value, and a fitness value greater than 100 will have a biological age less than their chronological age, while an individual with an energy quotient, metabolic rate value, resting fat metabolism value, exertional fat metabolism value, and a fitness value less than 100 will have a biological age greater than their chronological age.

In a preferred embodiment, a medical practitioner may prescribe a program of nutrition and exercise to decrease the biological age of the subject, where the subject's biological age is greater than their chronological age. The program is determined by the other metabolic factors (energy quotient, MRV, RFM, EFM, FV) as described and determined above and may include nutritional supplementation, dietary restrictions, hormonal replacement, medication, and a specified exercise regimen targeting the factors calculated above. The exercise regimen may include resistance training and/or aerobic training.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A method for analyzing the biological age of a subject comprising:

obtaining age, body fat percentage, weight and sex information from a subject;

measuring the subject's average oxygen consumption when the subject is at rest;

measuring the subject's average respiratory exchange ratio when the subject is at rest;

measuring the subject's average oxygen consumption when the subject's respiratory exchange rate is about 0.85;

measuring the subject's average oxygen consumption when the subject's respiratory exchange rate is about 1.00;

measuring the subject's average work produced when the subject's respiratory exchange ratio is about 1.00; and calculating the subject's biological age as a function of the subject's average oxygen consumption at rest, the subject's average respiratory exchange ratio when the subject is at rest the subject's average oxygen consumption when the subject's respiratory exchange rate is about 0.85, the subject's average oxygen consumption when the subject's respiratory exchange rate is about 1.00, and the subject's average work produced when the subject's respiratory exchange ratio is about 1.00;

wherein the calculation is dependent on the sex of the subject.

2. The method of claim 1 further comprising, prescribing a program of nutrition and exercise to treat the biological age of the subject.

3. The method of claim 1, wherein the calculation quantities the biological age as a number.

4. The method of claim 3 further comprising, prescribing a program of nutrition and exercise to decrease the biological age of the subject.

5. The method of claim 1, wherein the age of the subject is defined as an age in years.

6. The method of claim 5, wherein the age in years of a subject over a predetermined age is a default age and the age in years of a subject under the predetermined age is the subject's actual age.

7. A method for analyzing the biological age of a subject comprising:

obtaining age, body fat percentage, weight and sex information from a subject;

measuring the subject's average Oxygen consumption when the subject is at rest;

measuring the subject's average respiratory exchange ratio when the subject is at rest;

measuring the subject's average oxygen consumption when the subject's respiratory exchange rate is about 0.85;

measuring the subject's average oxygen consumption when the subject's respiratory exchange rate is about 1.00;

measuring the subject's average work produced when the subject's respiratory exchange ratio is about 1.00;

analyzing the subject's energy quotient, metabolic rate, resting fat metabolism, exertional fat metabolism and fitness value; and calculating the subject's biological age as a function of the subject's energy quotient, metabolic rate, resting fat metabolism, exertional fat metabolism and fitness value.

8. The method of claim 7 further comprising, prescribing a program of nutrition and exercise to treat the biological age of the subject.

9. The method of claim 7, wherein the biological age of the subject is quantified as a number.

10. The method of claim 9 further comprising, prescribing a program of nutrition and exercise to decrease the biological age of the subject.

11. The method of claim 7, wherein analyzing the subject's energy quotient comprises;
   calculating the subject's predicted maximum oxygen consumption based on the subject's sex, body fat percentage, weight and age in years;
   wherein the age in years of a subject over a predetermined age is a default age and the age in years of a subject under the predetermined age is the subject's actual age; and
   dividing the subject's average oxygen consumption when the subject's respiratory exchange rate is about 1.00 by the subject's predicted maximum oxygen consumption to obtain an energy quotient for the subject.

12. The method of claim 7, wherein analyzing the subject's metabolic rate comprises:
   calculating the subject's predicted basal metabolic rate based on the subject's sex, body fat percentage, weight and age in years;
   wherein the age in years of a subject over a predetermined age is a default age and the age in years of a subject under the predetermined age is the subject's actual age; and dividing the subject's average resting oxygen consumption by the subject's predicted basal metabolic rate to obtain a metabolic rate value for the subject.

13. The method of claim 7, wherein analyzing the subject's exertional fat metabolism comprises:
   calculating the subject's predicted maximum oxygen consumption based on the subject's sex, body fat percentage, weight and age in years;
   wherein the age in years of a subject over a predetermined age is a default age and the age in years of a subject under the predetermined age is the subject's actual age; and
   dividing the subject's average oxygen consumption when the subject's respiratory exchange rate is about 0.85by the subject's predicted maximum oxygen consumption to obtain the exertional fat metabolism for the subject.

14. The method of claim 7, wherein analyzing the subject's fitness value comprises:
   calculating the subject's predicted maximum oxygen consumption based on the subject's sex, body fat percentage, weight and age in years;
   wherein the age in years of a subject over a predetermined age is a default age and the age in years of a subject under the predetermined age is the subject's actual age;
   calculating the subject's predicted maximum work produced as a functional of the subject's predicted maximum average oxygen consumption; and
   dividing the subject's average work produced when the subject's exertional respiratory exchange ratio is about 1.00 by the subject's predicted maximum work produced to obtain a fitness value for the subject.

15. A method for analyzing the biological age of a subject comprising:
   obtaining age, body fat percentage, weight and sex information from a subject;
   measuring the subject's average work produced when the subject's exertional respiratory exchange ratio is about 1.00;
   calculating the subject's predicted maximum oxygen consumption based on the subject's sex, body fat percentage, weight and age in years;
   wherein the age in years of a subject over a predetermined age is a default age and the age in years of a subject under the predetermined age is the subject's actual age;
   calculating the subject's predicted maximum work produced as a function of the subject's predicted maximum oxygen consumption;
   dividing the subject's average work produced when the subject's exertional respiratory exchange ratio is about 1.00 by the subject's predicted maximum work produced to obtain a fitnesses value for the subject; and
   comparing the subject's fitness value to a target fitness value range fox the subject's appropriate age group.

16. The method of claim 15, wherein the predetermined age is equal to the default age 17. The method of claim 15, wherein a fitness value greater than the fitness value range for the subject's appropriate age group indicates decreased biological age.

18. The method of claim 15, wherein a fitness value lower than the fitness value range for the subject's appropriate age group indicates increased biological age.

19. The method of claim 15, wherein a fitness value equal to or higher than the target fitness value range indicates optimal strength and fitness.

20. The method of claim 15, wherein a fitness value lower than the target fitness value range indicates decreased strength and fitness.

21. The method of claim 15, wherein a fitness value significantly lower than the target fitness value range indicates decreased muscle mass.

22. The method of claim 21 further comprising, treating decreased strength and fitness by prescribing nutritional supplementation and an exercise regimen.

23. The method of claim 22, wherein the exercise regimen further comprises weight resistance training.

* * * * *